United States Patent [19]

Foster

[11] Patent Number: 4,681,601
[45] Date of Patent: Jul. 21, 1987

[54] BUBBLE INJECTION DISSOLVED GAS MEASUREMENT METHOD AND APPARATUS

[75] Inventor: Donald A. Foster, Lakeville, Mass.

[73] Assignee: Polaroid Corporation, Cambridge, Mass.

[21] Appl. No.: 566,230

[22] Filed: Dec. 28, 1983

[51] Int. Cl.$^4$ .............................................. B01D 19/00
[52] U.S. Cl. .......................................... 55/18; 55/36; 55/196; 55/270; 73/19; 261/121.1
[58] Field of Search ........... 73/19, 53, 861.41, 863.71; 261/76, 81, 121 R, DIG. 75; 55/18, 36, 159, 160, 196, 270

[56] References Cited

U.S. PATENT DOCUMENTS

| | | | |
|---|---|---|---|
| 2,745,282 | 5/1956 | Rochon | 73/19 X |
| 3,058,908 | 10/1962 | Morgan | 261/121 R X |
| 3,171,273 | 3/1965 | Dijkema | 73/19 |
| 3,942,792 | 3/1976 | Topol | 73/19 |
| 3,962,046 | 6/1976 | Morrison | 73/19 X |
| 4,314,969 | 2/1982 | Arthur et al. | 73/19 X |

FOREIGN PATENT DOCUMENTS

| | | | |
|---|---|---|---|
| 1085825 | 10/1967 | United Kingdom | 73/19 |
| 1446182 | 8/1976 | United Kingdom | 73/19 |

OTHER PUBLICATIONS

Article entitled, "Vibrating Capillary for Production of Small Uniform Bubbles" in publication, The Review of Scientific Instruments, vol. 38, No. 7, pp. 969-970, (Jul. 1967), by F. MacIntyre.

*Primary Examiner*—Robert Spitzer
*Attorney, Agent, or Firm*—John J. Kelleher

[57] ABSTRACT

A method and apparatus for indirectly measuring the percentage of dissolved gas in a process liquid by injecting bubbles of the same kind of gas of predetermined diameter into the liquid to be measured and then measuring gas bubble life or survival time. Bubble lifetime is directly related to dissolved gas percentage. A relatively long gas bubble lifetime would be indicative of a highly saturated or poorly degassed process liquid, whereas a relatively short bubble lifetime would be indicative of a low degree of saturation or a well degassed process liquid. In one embodiment, dissolved gas percentage is determined by placing a small quantity of the process liquid into a container, injecting a burst of gas bubbles, of predetermined size, into this quantity of liquid, and then measuring gas bubble lifetime. In another embodiment, a portion of the liquid being measured is continuously routed through a tube at a known constant flow rate. A continuous series of individual bubbles are then injected into the transparent tube, at a fairly constant rate, at or near the bottom thereof. The maximum distance attained by a bubble within the transparent tube before disappearing from view is a direct indication of the percentage of dissolved gas in the liquid being measured.

12 Claims, 3 Drawing Figures

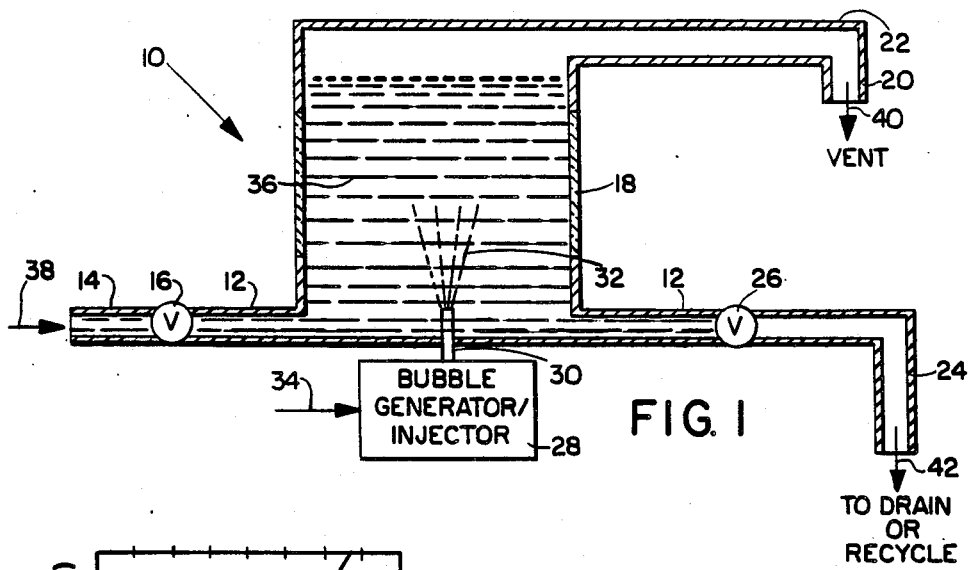
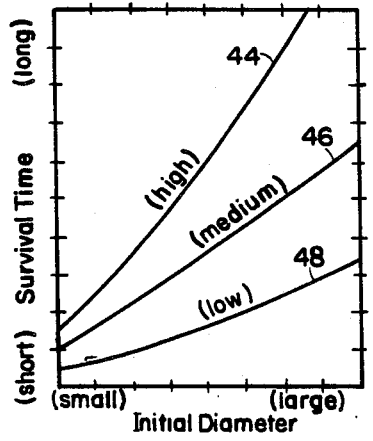
FIG. 3
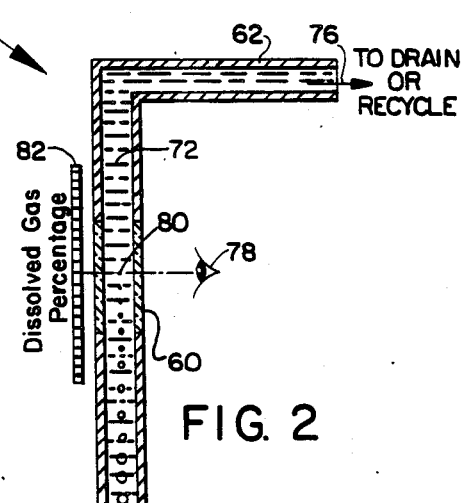
FIG. 2
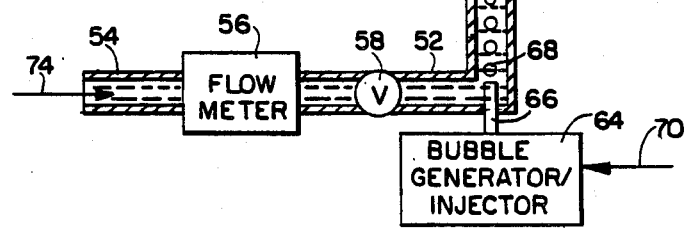

BUBBLE INJECTION DISSOLVED GAS MEASUREMENT METHOD AND APPARATUS

BACKGROUND OF THE INVENTION

The present invention relates to apparatus for measuring the percentage of dissolved gas in a liquid, in general, and to apparatus for rapidly and accurately measuring dissolved gas percentages in liquids moving within a conduit or similar enclosure, in particular.

The presence of dissolved gas in a liquid can produce any number of unwanted conditions in various manufacturing industries. In, for example, the photographic industry, the presence of dissolved gas in a coating fluid can have a decidedly negative impact on a finished photographic product. During the process of coating photographic films, for example, coating fluids are often subjected to pressures well in excess of and well below atmospheric pressure. If the coating fluid contains a significant amount of dissolved gas and this dissolved gas containing liquid is subjected to a low-enough negative pressure, the dissolved gas will come out of solution in the form of gas bubbles. Gas bubbles in a photographic film coating fluid creates voids in the coating fluid that show up as spots or imperfections in a finished photographic print. If the presence of dissolved gas in a photographic film coating fluid can be timely determined, steps can be taken to either remove any resulting gas bubbles or to preferably prevent the occurance of such gas bubbles by subjecting the dissolved gas containing coating fluid to conventional degassing techniques.

Several different techniques are presently available for measuring the percentage of dissolved gas in a liquid. However, each of these techniques suffers from one or more shortcomings that render them either unsuitable, inadequate or less than desirable for the dissolved gas measurement task presented.

In many applications it is desirable to have the percentage of dissolved gas rapidly and continuously measured. However, some gas measurement techniques involve the time-consuming task of extracting a sample of the liquid to be tested and then transporting same to a distant laboratory where the amount of dissolved gas is determined by observing bubble formation in the liquid while the liquid is being subjected to negative and positive pressures. Other techniques either employ apparatus that is not compatible with the liquid to be tested in that it might introduce contaminants into the liquid or are not capable of measuring the type of gas that is dissolved in same. Still other techniques produce unacceptably inaccurate measurements of dissolved gas percentages.

The primary object of the present invention is, therefore, to provide apparatus for rapidly and continuously measuring the percentage of dissolved gas in a liquid moving within a conduit.

Another object of the present invention is to provide apparatus for rapidly and continuously measuring the percentage of dissolved gas in a process liquid with a fairly high degree of accuracy.

A further object of the present invention is to provide a technique for measuring the percentage of dissolved gas in a process liquid that contaminates a minimum quantity of the liquid being measured.

Other objects, features and advantages of the present invention will be readily apparent from the following description of the preferred embodiment thereof taken in conjunction with the accompanying drawings.

SUMMARY OF THE INVENTION

In accordance with the present invention, apparatus is provided for indirectly measuring the percentage of dissolved gas in a liquid by injecting gas bubbles of the same kind of gas of constant predetermined diameter into said liquid and then measuring gas-bubble lifetime or survival time. Bubble lifetime is an indirect measure of the percentage of dissolved gas in the liquid into which said gas bubbles are injected. A relatively long gas bubble lifetime would indicate a highly saturated or poorly degassed liquid, whereas a relatively short bubble lifetime would indicate a low degree of saturation or a well degassed liquid. In one embodiment, a burst of gas bubbles is injected into a liquid sample with bubble lifetime subsequently being measured and in another embodiment, a series of individual bubbles are injected at a fairly constant rate into a continuously extracted liquid sample as said liquid sample moves at a constant predetermined flow rate. The maximum amount of movement attained by an individual bubble before disappearing from view is an indirect indication of the percentage of dissolved gas in the liquid in which said bubble is moving.

BRIEF DESCRIPTION OF THE DRAWINGS

FIG. 1 is a schematic diagram of process liquid sampling apparatus employing the batch mode, bubble burst dissolved gas measurement technique of the present invention.

FIG. 2 is a schematic diagram of process liquid sampling apparatus employing the continuously injected gas bubble dissolved gas measurement technique of the present invention.

FIG. 3 is a graph of gas bubble life as a function of the initial bubble diameter for a process liquid (water) at several different dissolved gas (air) saturation levels.

DESCRIPTION OF THE PREFERRED EMBODIMENTS

In FIG. 1 of the drawings, dissolved gas measurement apparatus 10 incorporating a preferred embodiment of the batch mode, bubble burst dissolved gas measurement apparatus of the present invention, is depicted. The apparatus includes conduit 12 connected to a source of process liquid (not shown) through portion 14 of said conduit 12 and manually operable process-liquid flow control valve 16. Measurement apparatus 10 also includes transparent process-liquid container 18 whose top portion is connected to vent 20 through conduit 22 and whose bottom portion is connected to conduit 12 in a pressure-tight relationship. The bottom portion of container 18 is also connected to a drain or to conventional process-liquid recycle apparatus (not shown) through output portion 24 of conduit 12, manually operable process liquid control valve 26 and said conduit 12.

Bubble generator/injector 28 includes gas bubble forming capillary or output tube 30 that projects into process liquid container 18 in a pressure-tight relationship. The output of said capillary tube 30 terminates within said container 18 at or near the bottom thereof. Bubble generator/injector 28 may be of the type described in an article entitled, "Vibrating Capillary for Production of Small Uniform Bubbles" in the publication "The Review of Scientific Instruments", Vol. 38, No. 7, pp 969-970 (July, 1967) by F. MacIntyre. Bubble generator/injector 28 is capable of generating a multiplicity or burst of equal size 32 in the approximate range of from a few hundred to a few thousand micrometers in diameter upon receipt of an external bubble generation/injection signal through path 34. Bubble generation/injection signals on path 34 are manually generated during the dissolved gas measurement process by conventional signal generating means capable of being readily initiated by an operator of dissolved gas measurement apparatus 10.

In operation, with process liquid control valve 26 in its closed position, process liquid control valve 16 is moved to its open position, thereby enabling process liquid 36 to flow in direction 38 from the main source of process liquid being tested (not shown), into transparent process liquid container 18. In this particular instance, the process liquid is water whose dissolved gas content must be fairly low for the use intended. As process liquid 36 enters said container 18, air within said container, displaced by said entering liquid, escapes in direction 40 through vent 20. When the level of process liquid entering container 18 reaches the desired height, valve 16 is moved to its closed position, thereby trapping process liquid sample 36 within container 18 and between liquid control valves 16 and 26. After valve 16 has been placed in its closed position, a bubble generation/initiation signal is applied to bubble generator/injection 28 through path 34.

At the instant that a bubble generation/injection signal is applied to path 34, conventional timing means are employed to measure the interval of time between the application of said signal to path 34 and bubble extinction. This time interval can be measured with a device that is as simple as a stop watch, or can be measured in a more sophisticated manner by a conventional electronic timer where the timer is started by the same signal that initiates bubble generation/injection and is stopped by an electronic signal from a conventional acoustical bubble sensor (not shown), for example, that senses when the bubbles become extinct or fully absorbed by the process liquid sample. After the percentage of dissolved gas in process liquid sample 36 has been determined, said liquid sample is drained from container 18 by opening valve 26. When valve 26 is placed in its open position, liquid sample 36 is routed to a temporary storage tank (not shown) through output portion 24 of conduit 12 in direction 42 for subsequent proper disposal or is routed to apparatus (also not shown) for restoring the sample process liquid to the condition existing prior to being subjected to a burst of dissolved gas measuring bubbles, if the value of the quantity of liquid sampled or other criteria dictates such processing.

Gas bubble lifetime or survival time is directly related to the percentage of dissolved gas in a liquid. There is a family of curves relating gas bubble survival time and initial bubble diameter to the percentage of dissolved gas in a particular liquid. Three mathematically calculated curves showing the approximate percentage of air in water for three different dissolved gas percentage levels are shown in drawing FIG. 3. Curves 44, 46 and 48 in said FIG. 3 are curves respectively indicating process liquids containing relatively high, medium and low percentages of a dissolved gas (air). As shown in FIG. 3, bubble survival time increases as the initial size of an injected bubble is increased. However, if the initial size of an injected gas bubble is held constant, there is a corresponding point on one of the curves of a family of curves such as those in FIG. 3 indicating the percentage of dissolved gas in a process liquid for a measured gas bubble lifetime. To determine the percentage of dissolved gas in a particular process liquid, a family of curves relating initial bubble diameter to bubble lifetime is developed for the particular process liquid to be measured either by mathematical calculation or by conventional laboratory techiques. By determining the location of a data point on a curve in said family of curves by knowing initial bubble diameter and bubble survival time, the percentage of dissolved gas in the liquid being measured is readily ascertained.

In FIG. 2 of the drawings, dissolved gas measurement apparatus 50 incorporating a preferred embodiment of the continuously injected gas bubble dissolved gas measurement technique of the present invention, is schematically illustrated. The technique employed with the apparatus of FIG. 2 produces a measurement of the percentage of dissolved gas in a process liquid considerably faster than such a measurement can be obtained when the dissolved gas measurement apparatus of FIG. 1 is employed. Apparatus 50 includes hollow tube 52 connected to a source of process liquid (not shown) through input portion 54 of said tube 52, flow meter 56 and manually operable process-liquid flow control valve 58. Tube 52 includes transparent vertical portion 60 for the upward passage of a liquid therethrough, and top portion 62 that is connected to a drain or to conventional process liquid recycle apparatus (not shown). Transparent portion 60 of tube 52 is preferably oriented in the vertical position shown, but may be employed in a horizontal position, especially if the liquid to be measured is highly viscous and the injected gas bubles have an extremely small diameter.

Bubble generator/injector 64 includes gas bubble forming capillary or output tube 66 that projects into the bottom of the vertical and partially transparent portion 60 of tube 52 in a pressure-tight relationship with the output of said capillary tube terminating at or near the bottom of said vertical tube portion. Bubble generator/injector 64 is similar to that described above in the above-mentioned article by F. MacIntyre with respect to bubble generator/injector 28 in drawing FIG. 1. Bubble generator/injector 64 is capable of generating a series of gas bubbles of equal initial size having a diameter in the vicinity of a few hundred micrometers, for an extended period of time, upon receipt of an external bubble generation/initiation signal, through path 70. A bubble generation/initiation signal on path 70 may be manually generated, but is preferably produced by a continuous series of pulses from a conventional pulse generator.

To activate dissolved gas measurement apparatus 50 of drawing FIG. 2, process-liquid flow control valve 58 is placed in its open position. With said valve 58 in its open position, process liquid sample 72 from the main source of process liquid being tested (not shown) flows through tube 52 in direction 74 through input portion 54 of tube 52, through flow meter 56, control valve 58 and then upward through transparent portion 60 of said tube 52. After passing through said transparent portion 60, process liquid sample 72 passes through output portion 62 of tube 52 in direction 76 where it is routed to a temporary storage tank (not shown) for proper disposal or is routed to apparatus (also not shown) for restoring said liquid sample to its pretest condition. Flow meter 56 controls the flow rate of liquid sample 72 moving within tube 52 to a predetermined and fairly constant flow rate. After the desired liquid flow rate has been established within tube 52, a bubble generation/initiation signal consisting of a continuous series of pulses is applied to bubble generator/injector 64 through path 70. Upon receipt of said signal, bubble generator/injector 64 injects a continuous series of air bubbles 68, of equal diameter, through an output tube or capillary 66 and into vertical transparent portion 60 of tube 52 at or near the bottom thereof. The type of gas injected (air) must be the same type of gas (air) that is dissolved in the liquid being measured. These injected bubbles move upward through said vertical tube portion partially because of the buoyant force on these bubble, but primarily due to the upward movement of liquid sample 72 through tube 52. As these injected gas bubbles move upward within tube 52, they are absorbed by said liquid sample at a rate that is proportional to the percentage of dissolved gas present in said liquid sample immediatley prior to be being injected by said gas bubbles. The lower the percentage of dissolved gas in the sampled liquid, the more rapid will be its absorption by the liquid sample. As explained above with respect to curves in the graph of drawing FIG. 3 and the dissolved gas measurement apparatus of FIG. 1, there is a direct, demonstrable relationship between the percentage of dissolved gas in a liquid and the diameter and survival time of a gas bubble injected or introduced into said liquid.

In order to measure the percentage of dissolved gas in a liquid sample at any time after apparatus 50 has been activated in the manner described above, a person 78 observes the maximum height 80 that any injected gas bubble attains with respect to scale 82 as it rises within transparent portion 60 of tube 52. Scale 82 is calibrated with respect to the type of liquid (temperature, viscosity, etc.) in liquid sample 72 and the rate at which said liquid sample moves through tube 52. With a continuous stream of equal diameter gas bubbles moving at a constant rate through conduit 52, the percentage of dissolved gas in the sampled liquid is continuously indicated in the above-described manner by the dissolved gas measurement apparatus shown in drawing FIG. 3.

It will be apparent to those skilled in the art from the foregoing description of my invention that various improvements and modifications can be made in it without departing from its true scope. The embodiments described herein are merely illustrative and should not be viewed as the only embodiments that might encompass my invention.

What is claimed is:

1. Apparatus for rapidly and accurately measuring the percentage of dissolved gas in a liquid, said apparatus comprising:
   means for sampling a portion of said liquid;
   means for generating a multiplicity of gas bubbles of equal diameter and of the same type as the dissolved gas and for introducing said bubbles into said liquid sample; and
   means for determining the length of time gas bubbles survive within said liquid sample from the time of initial introduction of a bubble until it is absorbed by said liquid sample to thereby determine the percentage of dissolved gas in said liquid.

2. Apparatus for rapidly and accurately measuring the percentage of dissolved gas in a liquid moving within a conduit, said apparatus comprising:
   a container for temporarily holding a sample of said liquid;
   means for directing a sample of said liquid within said container
   means for injecting a short burst of gas bubbles of equal diameter, and of the same type as the dissolved gas, into said liquid sample; and
   means for measuring the length of time the burst of gas bubbles survive within said liquid sample from the time of initial introduction until said burst of bubbles is substantially absorbed by said sampled liquid to thereby establish a data point on a curve in a family of curves relating initial bubble diameter and bubble lifetime to the percentage of dissolved gas in the liquid into which said multiplicity of gas bubbles have been injected.

3. The apparatus of claim 2 wherein said container is at least partially transparent and the point in time when said bubbles are fully absorbed by said liquid sample is determined by visually observing said liquid through a transparent portion of said container to determine when said injected bubbles vanish from view, which thereby establishes the said point in time when said bubbles are fully absorbed by said liquid sample.

4. The apparatus of claim 2 wherein the point in time when said bubbles are fully absorbed by said liquid sample is determined by an acoustical type bubble detector.

5. The apparatus of claim 2 wherein the diameter of equal diameter gas bubbles generated by said gas bubble generator are between 100 and 1000 micrometers.

6. Apparatus for rapidly, accurately and continuously measuring the percentage of dissolved gas in a liquid moving within a conduit, said apparatus comprising:
   a hollow tube, at least partially transparent, having both an inlet and an outlet, for directing a sample of said liquid therethrough;
   means for coupling the inlet of said tube to said liquid containing conduit and the outlet of said tube to a liquid drain or to liquid sample recycling apparatus;
   means for maintaining the flow rate of liquid moving through said hollow tube at a predetermined constant flow rate;
   means for generating and injecting a continuous series of gas bubbles, of equal diameter and of the same type of gas as the dissolved gas, into said hollow tube at a predetermined location; and
   a scale immediately adjacent said tube having dissolved gas indicating graduations thereon calibrated for dissolved gas percentage for the particular liquid moving within said hollow tube and its rate of movement therethrough for determining the percentage of dissolved gas in said liquid sample by measuring the maximum distance attained by an injected gas bubble with respect to said scale as said bubble moves through a transparent portion of said tube past said adjacent scale just before disappearing from view to thereby determine the percentage of dissolved gas in said liquid moving within said conduit.

7. The apparatus of claim 6, wherein said hollow tube directs said liquid sample in a generally upward direction, said gas bubbles are injected into said hollow tube near the bottom portion thereof and the maximum distance attained by an injected gas bubble is the maximum height in said generally upward direction.

8. Apparatus for measuring the percentage of dissolved gas in a liquid, said apparatus comprising:
a conduit having an inlet and an outlet;
means for directing a sample of said liquid through said conduit at a constant flow rate;
means for injecting a stream of gas bubbles of given size and of the same type of gas as the dissolved gas into said sample at a given point along said conduit; and
means downstream of said point of injection for determining the termination point of said stream of bubbles along said conduit and for providing a measure of the length between said injection point and termination point whereby in accordance with said constant flow rate the survival time of said bubbles and consequently the percentage of dissolved gas can be determined.

9. A method of rapidly and accurately measuring the percentage of dissolved gas in a liquid, comprising the steps of:
sampling a portion of said liquid;
generating a multiplicity of gas bubbles of equal diameter, and of the same type of gas as that of the dissolved gas, and introducing said bubbles into said liquid sample; and
determining the length of time gas bubbles survive within said liquid sample from the time of initial introduction until the bubble is absorbed by said liquid sample to thereby determine the percentage of dissolved gas in said liquid.

10. A method of rapidly and accurately measuring the percentage of dissolved gas in a liquid moving within a conduit, comprising the steps of:
establishing a container for temporarily holding a sample of said liquid;
diverting a sample of said liquid within said container;
injecting a short burst of gas bubbles of equal diameter into said liquid sample; and
measuring the length of time the burst of gas bubbles survive within said liquid sample from the time of initial introduction until said bubbles are absorbed by said sampled liquid to thereby establish a data point on a curve in a family of curves relating initial bubble diameter and bubble lifetime to the percentage of dissolved gas in the liquid into which said multiplicity of gas bubbles have been injected.

11. A method of rapidly, accurately and continuously measuring the percentage of dissolved gas in a liquid moving within a conduit, comprising the steps of:
providing a hollow tube, at least partially transparent, having both an inlet and an outlet, for directing a sample of said liquid therethrough;
coupling the inlet of said tube to said liquid containing conduit and the outlet of said tube to a liquid drain or to liquid sample recycling apparatus;
means for maintaining the flow rate of liquid moving through said hollow tube at a predetermined constant flow rate;
injecting a continuous series of gas bubbles, of equal diameter, and of the same type of gas as that of the dissolved gas, into said hollow tube at a predetermined location;
establishing a scale immediately adjacent the said transparent portion of said tube with dissolved gas indicating graduations thereon calibrated for dissolved gas percentage for the particular liquid moving within said hollow tube and its rate of movement therethrough; and
measuring the maximum distance attained by an injected gas bubble with respect to said scale as said bubble moves through the said transparent portion of said tube past said adjacent scale just before disappearing from view to thereby determine the percentage of dissolved gas in said liquid moving within said conduit.

12. The method of claim 11, wherein said hollow tube directs said liquid sample in a generally upward direction, said gas bubbles are injected into said hollow tube near the bottom portion thereof and the maximum distance attained by an injected bubble is the maximum height in said generally upward direction.

* * * * *